(12) United States Patent
Lenke et al.

(10) Patent No.: US 7,641,778 B2
(45) Date of Patent: Jan. 5, 2010

(54) GEL ELECTROELUTION AND SAMPLE SEPARATION DEVICES AND ASSOCIATED PROCESSES

(75) Inventors: James H. Lenke, Morgantown, WV (US); Matthew Powell, Morgantown, WV (US)

(73) Assignee: Protea Biosciences, Inc., Morgantown, WV (US)

( * ) Notice: Subject to any disclaimer, the term of this patent is extended or adjusted under 35 U.S.C. 154(b) by 344 days.

(21) Appl. No.: 11/655,440

(22) Filed: Jan. 19, 2007

(65) Prior Publication Data

US 2007/0221834 A1    Sep. 27, 2007

Related U.S. Application Data

(63) Continuation-in-part of application No. 11/388,193, filed on Mar. 23, 2006, now abandoned.

(51) Int. Cl.
*G01N 27/447* (2006.01)
(52) U.S. Cl. .................................. 204/462; 204/613
(58) Field of Classification Search ................ 204/462, 204/466, 600, 606, 613, 615, 616
See application file for complete search history.

(56) References Cited

U.S. PATENT DOCUMENTS

| | | | |
|---|---|---|---|
| 4,160,161 A | 7/1979 | Horton | |
| 4,861,988 A | 8/1989 | Henion et al. | |
| 5,635,045 A | 6/1997 | Alam | |
| 5,800,202 A | 9/1998 | Tsuji et al. | |
| 5,840,169 A | 11/1998 | Andersen | |
| 5,858,195 A | 1/1999 | Ramsey | |
| 6,462,337 B1 | 10/2002 | Li et al. | |

(Continued)

FOREIGN PATENT DOCUMENTS

WO    WO 2004/017040 A2    2/2004

OTHER PUBLICATIONS

Papadopoulos, Vassiliois, "Identification and purification of a human Sertoli cell-secreted protein (hSCSP-80) stimulating Leydig cell steroid biosynthesis", Journal of Clinical Endocrinology and Metabolism (1991), 72(6), 1332-9.

(Continued)

*Primary Examiner*—Kiet T Nguyen
(74) *Attorney, Agent, or Firm*—K & L Gates LLP

(57) ABSTRACT

A gel electroelution device can have a gel spot column having upstream and downstream openings in fluid communication with an inlet and outlet, respectively. The gel spot column receives a gel spot and negative and positive electrodes are fluid communication with the inlet and outlet, respectively. A gel electroelution process can involve flowing a buffer solution through the gel spot in a first direction, and creating an electric field across the gel spot in the same direction. A separator device can have a generally cylindrical collection reservoir in fluid communication with inlet, filtrate, and retentate ports, a filter intermediate the inlet and filtrate ports. The inlet and retentate ports can intersect the collection reservoir in a manner to induce a cyclonic flow. A flow separation process can involve inducing a generally cyclonic flow in the collection reservoir, and filtering the fluid therein to retain the retentate.

12 Claims, 6 Drawing Sheets

U.S. PATENT DOCUMENTS

| | | |
|---|---|---|
| 6,481,648 B1 | 11/2002 | Zimmermann |
| 6,737,640 B2 | 5/2004 | Kato |
| 6,800,202 B2 | 10/2004 | Moon et al. |
| 7,060,975 B2 | 6/2006 | Seaward et al. |
| 7,070,682 B2 * | 7/2006 | Lee et al. .................... 204/462 |

OTHER PUBLICATIONS

Dunn, Michael J., Electroelution of proteins from polyacrylamide gels. Chapter 33, pp. 357- 362 of Methods in Molecular Biology, Humana, Totowa, New Jersey, (1996).

Jin, Wen-Hai, et al., Human Plasma Proteome Analysis by Multidimensional Chromatography Prefractionation and Linear Ion Trap Mass Spectrometry Identification, Journal of Proteome Research (2005), 4(2), 613-619.

Georgiou, Harry M., et al., Proteomic analysis of human plasma: failure of centrifugal ultra-filtration to remove albumin and other high molecular weight proteins, Proteomics (2001), 1(12), 1503-1506.

Apffel, Alex, Multidimensional chromatography of intact proteins. Chapter 4, p. 75-100 of Purifying Proteins for Proteomics, Cold Spring Harbor Laboratory Press, Woodbury, NY (2004).

Muddiman, David, et al., "Multidimensional chromatography ESI-FT-ICR mass spectrometry: the ultimate peak capacity for proteome measurements", Abstracts, $35^{th}$ Central Regional Meeting of the American Chemical Society, Pittsburgh, PA, United States, Oct. 19-22 (2003), 10.

* cited by examiner

GEL ELECTROELUTION AND SAMPLE SEPARATION DEVICES AND ASSOCIATED PROCESSES

RELATED APPLICATIONS

This application is a continuation-in-part of U.S. patent application Ser. No. 11/388,193, filed Mar. 23, 2006 now abandoned.

BACKGROUND

A fundamental difficulty in protein research is the ability to efficiently extract proteins from SDS-PAGE (sodium dodecyl sulfate polyacrylamide gel electrophoresis) gels following electrophoretic separations. Gel electrophoresis separates proteins on the basis of molecular weight and size. An electric field applied across the gel assists in the transit of the proteins through the sieve-like pores of the gel matrix. After the electrophoretic separation is finished, the gels are often "fixed" through a chemical treatment of the gel to prevent the solvated proteins from diffusing within the gel. The fixing solution contains organic solvent (e.g. methanol or ethanol) and acidic modifiers (e.g. acetic or formic acid) that induce a precipitation of the proteins within the gel matrix, which effectively inhibits the proteins from diffusing from their position. Subsequent staining of the fixed proteins with silver or Coomassie stains permits visualization of the separated protein gel bands. While fixation is important for maintaining the resolution of the gel separation over time, the process greatly reduces the ability of downstream chemical analysis of the proteins due to their insoluble nature.

Two common types of sample preparation methods exist for downstream analysis of gel separated proteins: enzymatic digestion for protein identification analyses and extraction of the intact protein. In protein identification experiments, the proteins are digested in-gel using proteolytic enzymes (e.g. trypsin, endoproteinase Glu-C, Arg-C, Lys-C). Following digestion, the resultant peptide mixtures are extracted from the gel matrix for subsequent analysis by HPLC-MS/MS, or chromatographic separation of the peptide mixtures coupled on-line with detection by tandem mass spectrometry, for collection of peptide MS/MS spectra that are used in database correlation analysis for protein identification. Alternatively, the proteins can be extracted intact from the gel matrix and used in a variety of downstream analyses, such as direct infusion mass spectrometry or matrix assisted laser desorption ionization (MALDI) mass spectrometry experiments for determination of molecular weight. In both cases, the precipitated nature of the proteins in fixed gels impedes the collection of the peptide digest mixtures or intact proteins from the gel. Extraction of the samples is achieved through repeated rinses of the gel bands, which heavily relies on diffusion of the analytes into the extraction solution. The precipitated nature of the proteins also impedes digestion by reducing the enzyme activity, as compared to digestion of soluble protein molecules. Effectively, the gel matrix is useful for electrophoretic separation of proteins mixtures, but hampers downstream analysis of the protein analytes.

Currently, techniques for extraction of the proteins from the excised gel band involve repetitive extraction rinses, followed by drying down of the collected rinsed to remove the solvent. Generally, this method relies on diffusion of the protein molecules out of the gel matrix and into the extraction solvent. Because of their large size relative to the dimensions of the gel pores, this technique is very limited for the extraction of intact proteins from the gel matrix. Fixation of the proteins further compounds the problem. Peptide digests can be extracted with greater success due to their smaller size, but the process remains diffusion-limited. Alternatively, excised gel bands have been minced up using homogenizers to increase the surface area of the gel band for extraction. While homogenization improves diffusion-limited extraction, it also introduces potential contamination of the sample and can create ultrafine gel particles that are also collected in the extraction rinses and impede downstream analyses. Additionally, homogenization does not alleviate the solubility problems associated with fixed proteins.

Electroelution is a technique that utilizes the application of an electric field to induce migration of the proteins in a gel band into solution. Conventional methods of extracting gel-separated proteins using electroelution are believed to have been largely unsuccessful and/or non-reproducible for a variety of reasons. Electroelution is most effective for the extraction of solubilized proteins, and chemical fixation of proteins during staining greatly hampers the electroelution process. Electroelution requires the application of an electric field across the excised gel band, and the tiny, asymmetric nature of the gel piece presents inherent problems for fabrication of an electroelution device. After electroelution from the gel piece, proteins are free to adsorb onto surfaces of the electroelution device or on the surface of the gel. Lastly, collection of extracted proteins by such methods can be largely inefficient because the proteins are often diluted into larger volumes of solvent. Adsorption losses during extraction and collection, coupled with transport/handling losses and contamination, can reduce the overall efficiency of the electroelution process and negatively impact the reproducibility.

Accordingly, there is a need for an electroelution process and device to reproducibly and efficiently extract electrophoretically separated intact proteins from an SDS-PAGE gel matrix.

Biological solutions are often comprised of a dilute mixture of the analytes of interest, other similar chemical species, chemical contaminants, and bulk solvent molecules. Sample preparation of these solutions can thus require the concentration of the analytes (i.e., proteins) and purification of the analyte from the mixture. Conventional methods of concentrating the sample solution often utilize a porous membrane filter possessing a characteristic molecular weight cut-off (MWCO). Molecules of a size below the MWCO of the membrane pass through the pores and constitute the filtrate, while molecules of a size above the MWCO of the membrane are retained by the membrane as the retentate. Following concentration of a solution, the retentate can be purified through dilutional rinses using a buffer solution that is free of the chemical contaminants, and re-concentration of the retentate. Additionally, the retentate composition can be changed through solvent exchange rinses and re-concentration of the retentate solution.

While simple in concept, the concentration and purification of protein samples through the use of MWCO ultrafiltration (UF) membranes can be difficult to perform reproducibly and effectively on the bench top. Traditionally, centrifugal tubes containing the MWCO membranes are utilized. The sample solution is loaded onto the membrane surface in the upper retentate reservoir of the centrifugal ultrafiltration tube. A centrifuge is used to provide a gravitational driving force to push the solvent through the membrane filter and into the filtrate reservoir. Membrane fouling is a major problem for these devices, as particles can clog the pores of the membrane, resulting in decreased flow and increased adsorption of species onto the cloggants. Additionally, the recovery yield can be significantly affected, as recovery of sample proteins adsorbed onto the device surfaces and MWCO membrane can be difficult and poorly reproducible. Sample recovery can involve manual pipetting (Pall NanoSep and MicroSep devices) or inversion of the retentate reservoir and centrifugal collection of the sample (Millipore Ultrafree-MC and -CL devices).

Centrifugal ultrafiltration devices can be run in parallel, as many of the units can be spun in a centrifuge simultaneously. However, these centrifugal UF devices are very labor-intensive, as each step of sample addition, filtrate removal, rinse solution addition, and retentate recovery require manual manipulation of each device. Thus, the cumulative efforts for concentration and purification of a large number of samples can become time and labor intensive, and there can also be increased opportunities for contamination and handling/transfer losses.

Accordingly, there is a need for a sample separation process and device to assist researchers in the concentration, purification, and preparation of protein samples for analysis.

SUMMARY

An embodiment of a gel electroelution device can generally comprise a gel spot column having upstream and downstream openings, wherein the gel spot column is adapted to receive a gel spot containing proteins to be extracted therefrom, an inlet in fluid communication with the upstream opening of the gel spot column, an outlet in fluid communication with the downstream opening of the gel spot column, a negative electrode in fluid communication with the inlet, a positive electrode in fluid communication with the outlet, and wherein the positive and negative electrodes can be operated to create an electric field across the gel spot in the same direction as a flow of buffer solution from the inlet through the outlet in order to electrophoretically migrate the proteins out of the gel spot and into the buffer solution. Additional embodiments of the gel electroelution device can further comprise a frit plug intermediate the gel spot and the outlet, and a purge line in fluid communication with the gel spot column intermediate the gel well and the outlet. In still further embodiments, the gel electroelution device can comprise a housing, with the gel spot column removably enclosed in the housing, and wherein the gel spot column further comprises a gel spot cutter, such that when the gel spot cutter is used to cut a gel spot, the gel spot is retained in the gel spot cutter, and the gel spot cutter is then enclosable in the housing with the gel spot retained therein.

An embodiment of a gel electroelution process to extract electrophoretically separated intact proteins from a gel matrix can generally comprise immobilizing a gel spot from the gel matrix (the gel spot containing the proteins to be extracted) flowing a buffer solution through the gel spot in a first direction, and creating an electric field across the gel spot in the first direction such that the proteins electrophoretically migrate out of the gel spot and into the buffer solution. In additional embodiments of the gel electroelution process, admixing of flow upstream and downstream of the gel spot can be prevented, the gel matrix can be an SDS-PAGE gel matrix, and the buffer solution can mimic a natural running buffer of the SDS-PAGE gel separation. In further embodiments of the gel electroelution process, the buffer solution can be filtered downstream of the gel spot to remove particles of gel, and migrated proteins can be collected in a reservoir or solid phase extraction trapping column.

An embodiment of a separator device can generally comprise a collection reservoir in fluid communication with an inlet port, a filtrate port, and a retentate port, and a filter intermediate the inlet port and the filtrate port. In additional embodiments, the separator device can have a generally cylindrical collection reservoir and each of the inlet port and retentate port can intersect the collection reservoir in an off-center, generally orthogonal orientation such that a cyclonic flow is induced in the collection reservoir. In further embodiments, the inlet, retentate and filtrate ports can be marked with different colors to easily and quickly distinguish the different ports.

An embodiment of a flow separation process can generally comprise flowing a fluid sample into collection reservoir, inducing a generally cyclonic flow in the collection reservoir, filtering the fluid sample using hydrodynamic pressure created in the collection reservoir, and retaining retentate in the collection reservoir. Additional embodiments of the separation process can further comprise flowing a solution into the collection reservoir containing the retentate, and flowing the solution and retentate out of the collection reservoir for further processing, analysis, or storage. Further embodiments of the process can comprise rinsing, desalting, purifying, and/or concentrating the retentate in the collection reservoir, and fluorescent labeling of the retentate in the collection reservoir can also be performed.

The gel electroelution device and the separator device can used individually, or can be combined into an integrated stand-alone device. The selective fluid communication both between the two devices and between the individual ports on each device, can be governed by one or more switching valves and associated electronics, such as a control panel, for example, an LCD touch screen, all of which can be governed by a computer, such as a personal computer. In this manner, for example, a sample can be processed in the gel electroelution device and then transferred directly to the separator device for further processing therein without exposing the sample to external sources or contamination.

Other details, objects, and advantages of the gel electroelution and separator processes and associated devices will become apparent from the following detailed description and the accompanying drawings figures of certain embodiments thereof.

BRIEF DESCRIPTION OF THE DRAWING FIGURES

A more complete understanding of the gel electroelution and sample separation processes and devices can be obtained by considering the following detailed description in conjunction with the accompanying drawing figures, in which.

DESCRIPTION OF CERTAIN EMBODIMENTS

Figure 1:
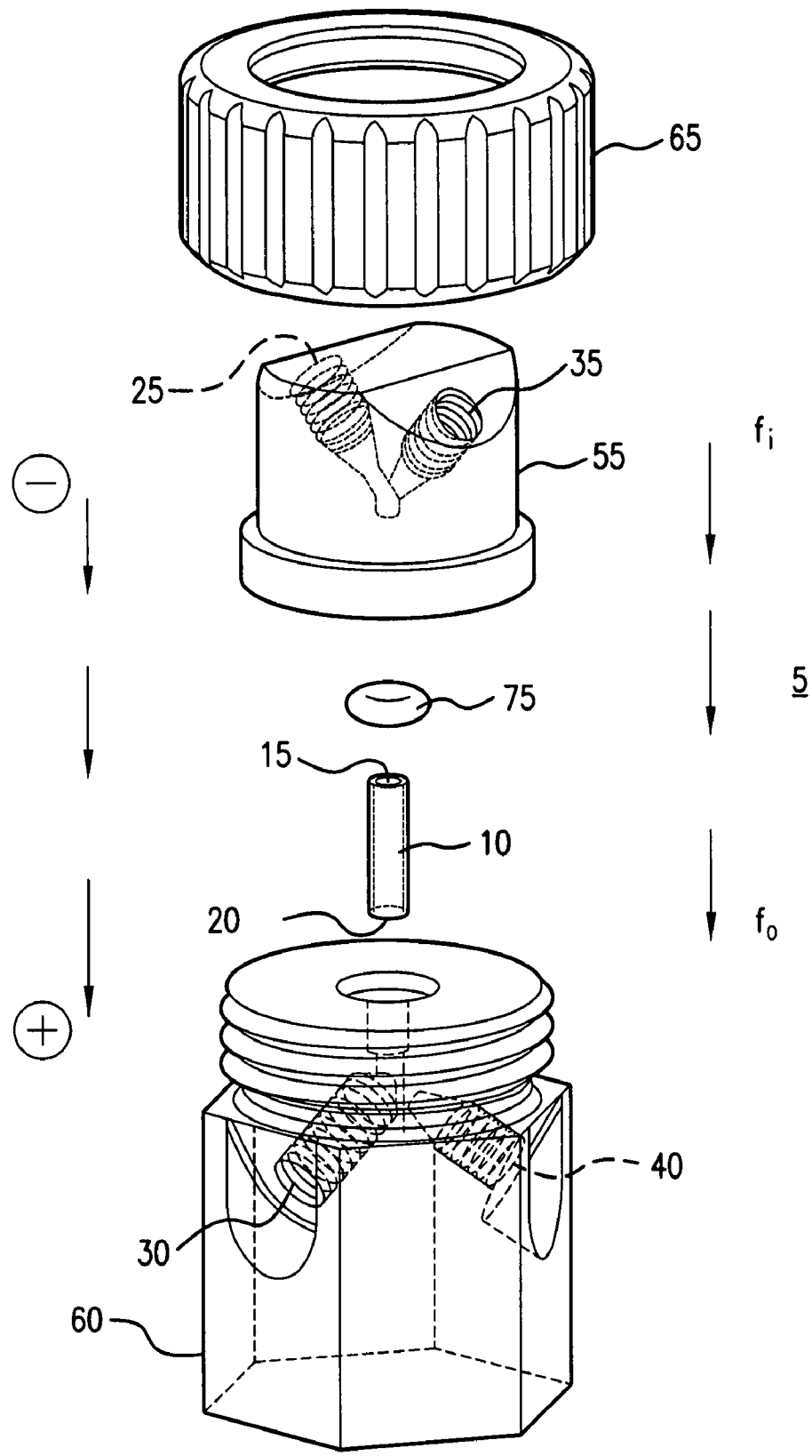
FIG. 1 is an exploded, front perspective view of an embodiment of a gel electroelution device.
Figure 2:
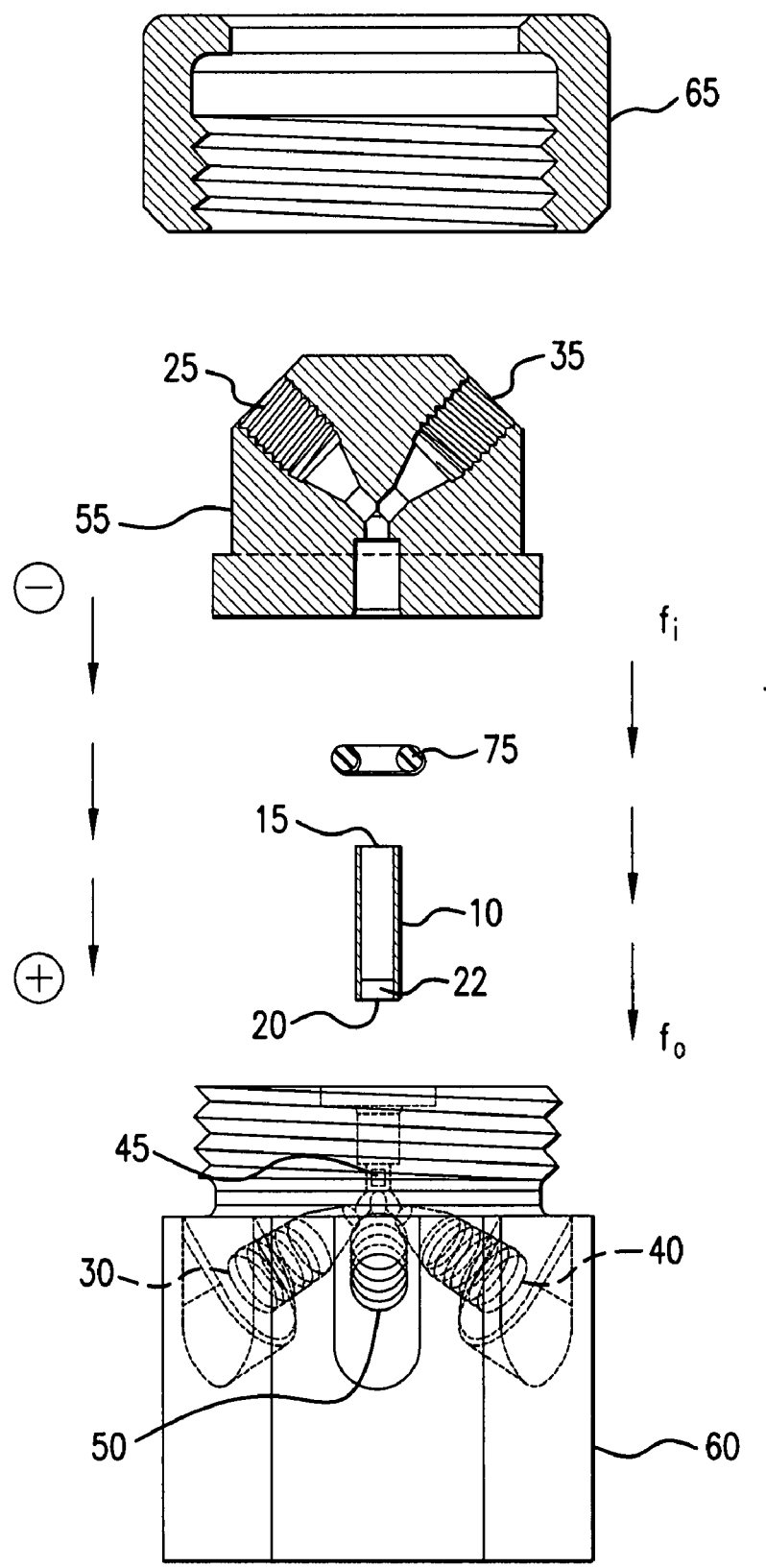
FIG. 2 is an exploded, rear perspective view of the gel electroelution device shown in FIG. 1.
Figure 3:
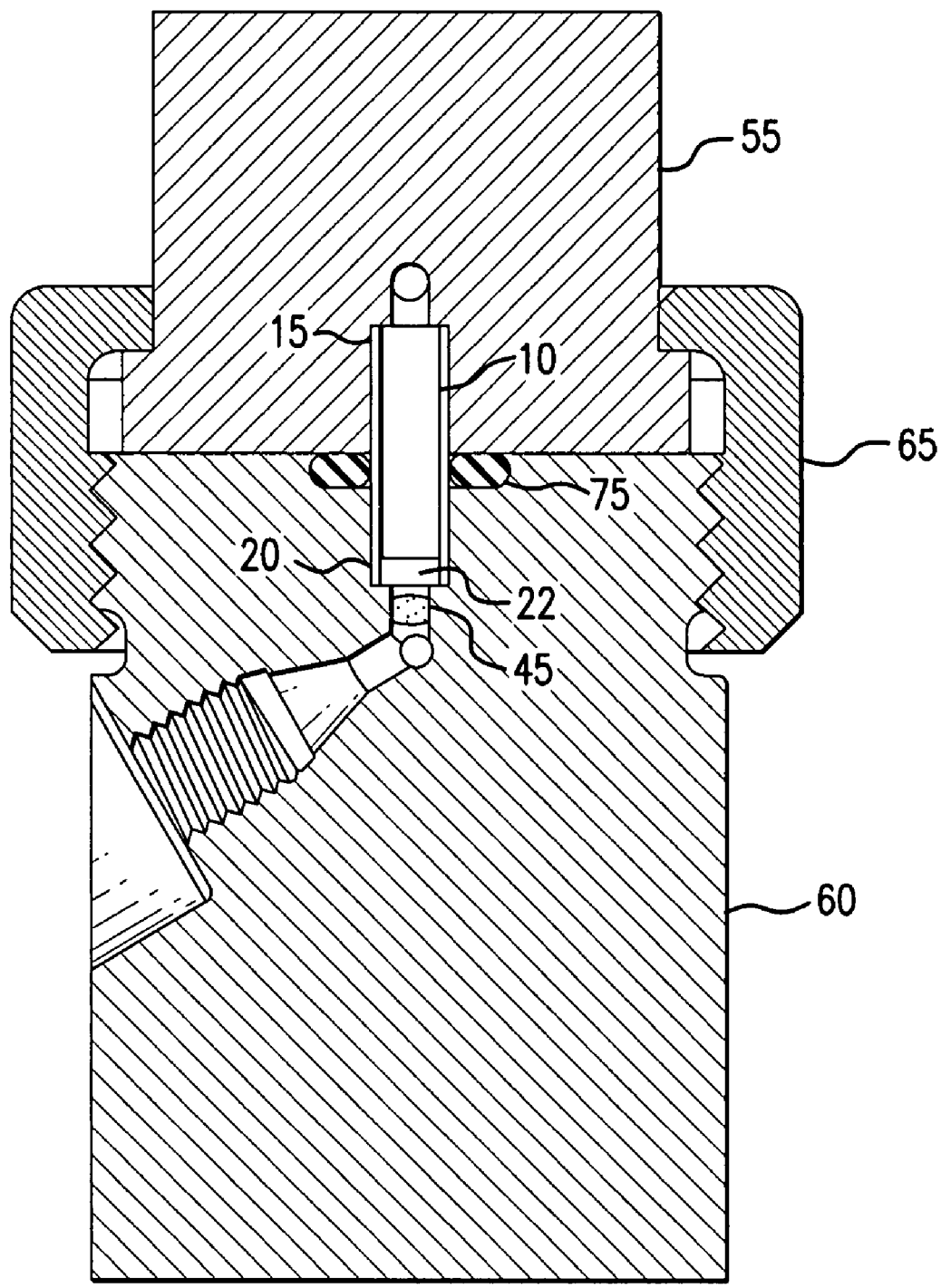
FIG. 3 is a side sectional view of the gel electroelution device shown in FIG. 1.

Referring now to the drawing figures, in which like reference numbers refer to like elements, FIGS. 1 through 3 illustrate an embodiment of a gel electroelution device 5 which can generally comprise a gel spot column 10 having upstream 15 and downstream 20 openings, wherein the gel spot column 19 is adapted to receive a gel spot 22 (see FIGS. 2 and 3) containing proteins to be extracted therefrom, an inlet 25 in fluid communication with the upstream opening 15 of the gel spot column 10, an outlet 30 in fluid communication with the downstream opening 20 of the gel spot column 10, a negative electrode receptacle 35 in fluid communication with the inlet 25, a positive electrode receptacle 40 in fluid communication with the outlet 30, and wherein positive and negative electrodes (not shown) can be inserted in such receptacles 35, 40 and operated to create an electric field across the gel spot 22 in the same direction, shown by arrows from (−) to (+), as a flow of buffer solution, shown by arrows from $f_i$ to $f_o$. In this way the proteins are electrophoretically migrated out of the gel spot 22 and into the buffer solution. The positive and negative electrodes (not shown) can be conventional, such as a simple conductor connected to a source of electricity. The gel electroelution device 5 can further comprise a frit plug receptacle 45 intermediate the gel spot and the outlet 30, for retaining a frit plug 75 therein, (see FIGS. 2 and 3) and a second fluid inlet 50, which can be, for example, a purge line. The frit plug 45 can prevent micron sized particles of gel from traveling downstream. Frit plugs 45 are well known in the art, and are commercially available from a number of suppliers. The purge line 50 can be used, for example, to remove air bubbles. Access to each of the inlets 25, 50 and the outlet 30 can be controlled in a conventional manor, such as by appropriate valves (not shown). Also, a plug (note shown) could be used, for example, if the second inlet 50 were a purge line. The gel electroelution devices can further comprise a housing made up of upper 55 and lower 60 portions which can be connected together, for example, using a cap 65, with the gel spot column 10 removably enclosed therein. The gel spot column 10 can further comprise a gel spot cutter, such that when used to cut a gel spot 22, the gel spot 22 is retained in the gel spot column 10, for example at the downstream end 20 thereof. The gel spot column 10 can then be enclosed in the housing between the upper 55 and lower 60 portions, with the gel spot 22 retained therein. In this manner the potential for contamination can be greatly reduced by not having to remove the gel spot 22 from the cutter. The gel electroelution device 5 can also have an o-ring 75 to provide a water tight seal between the gel spot column 10 and the housing.

Figure 4:
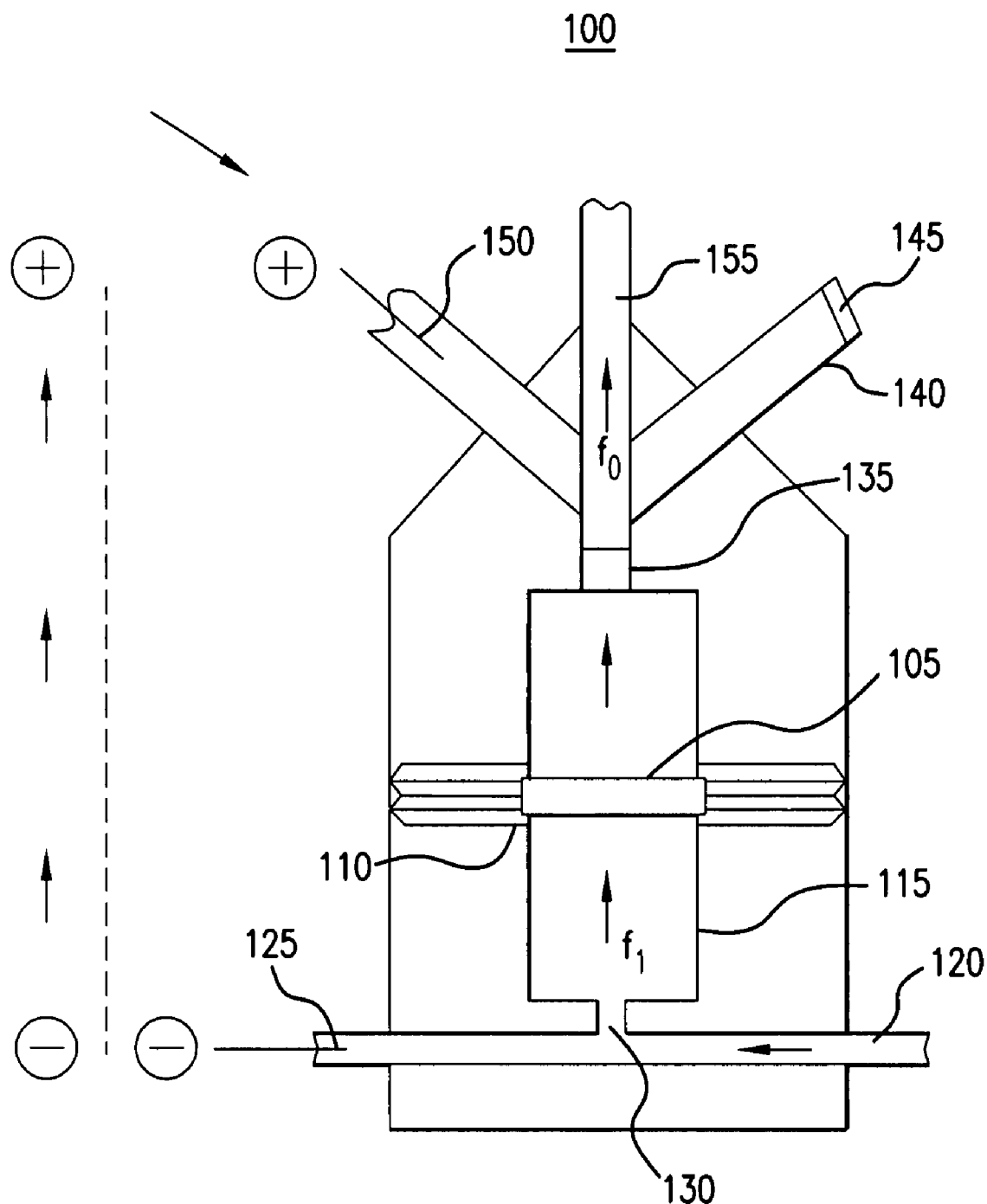
FIG. 4 is a side sectional view of another embodiment of a gel electroelution device.

Referring now to FIG. 4, another embodiment of a gel electroelution device 100 is illustrated in side sectional view. In this case, a gel spot 105 can be cut with any type of tubular spot picker (similar to using a plastic straw to cut gelatin). The gel spot 105 can be placed within a gel spot well 110, in the gel spot column 115. Upstream of the gel spot 105 is the inlet 120, and adjacent the inlet 120 is a sealed negative electrode 125. Fluid, for example a buffer solution without additional sample components, flows from the inlet 120 to the gel spot column inlet 130 and from there through the gel spot 105 to and through a frit plug 135. Downstream of the frit plug 135 can be a purge line 140 which can terminate in a purge line plug 145. Adjacent the purge line 140 is a sealed positive electrode 150. As shown by the arrows from (−) to (+), the electric field forms in the same direction as the fluid flow, as shown by the arrows from $f_i$ to $f_o$, and the protein band already having been determined to be of interest is electrophoretically migrated out of the gel spot 105 and into the flow through buffer. The flow through buffer then carries the extracted proteins through the frit plug 135 and further downstream to any desired separation or preparation component via the outlet 155. It should be noted that prior art static tubes for gel spot electroelution never enjoyed the continuous flow advantage of the gel electroelution device 100. Also, with the gel spot 105 having a diameter which leaves no gap between the gel spot 105 and the gel spot well 125 (which is shown as an annular recess in the wall of the gel spot column 115), separations are enhanced as contrasted with prior art gel eluting tubes which allowed space between the gel spot and the tube wall, and resulting admixing of upstream and downstream flows. Additionally, a sweep line can be configured to the purge line 140 to provide additional flow for removal of any protein sample remaining within the outlet 155.

An embodiment of a gel electroelution process to extract electrophoretically separated intact proteins from a gel matrix can generally comprise excising a gel spot from the gel matrix (in which the gel spot contains the proteins desired to be extracted), flowing a buffer solution through the gel spot in a first direction, and creating an electric field across the gel spot in the same direction, such that the proteins electrophoretically migrate out of the gel spot and into the buffer solution. In additional embodiments of the gel electroelution process, admixing of flow on upstream and downstream sides of the gel spot can be prevented, the gel matrix can be an SDS-PAGE gel matrix, and the buffer solution can mimic a natural running buffer of the SDS-PAGE gel separation. In further embodiments of the gel electroelution process, the buffer solution can be filtered downstream of the gel spot, for example using the aforesaid frit plug, to remove particles of gel, and migrated proteins can be collected in a reservoir or solid phase extraction trapping column.

The gel electroelution process and devices described herein can fill a perceived need in biological research—the ability to reproducibly and efficiently extract electrophoretically separated intact proteins from an SDS-PAGE gel matrix. The design of the gel electroelution process and devices can incorporate a combination of electroelution and hydrodynamic flow to permit the successful, reproducible extraction of gel-separated proteins. Following electrophoretic separation of proteins on an SDS-PAGE gel, the proteins are visualized using a non-fixing stain (i.e., modified Coomassie or SYPRO orange stain). The protein bands can be excised from the gel using a tubular spot picker, which is then inserted into the gel electroelution body, such as by inserting the aforesaid gel spot column containing the gel spot. The gel electroelution process/device then uses a low applied voltage and flow through buffer solution to establish an electric field across the gel spot in the same direction as the follow of buffer solution. The protein band electrophoretically migrates out of the gel and into the flow through buffer, which carries the extracted proteins out of the gel spot. The gel electroelution process/device design, incorporating electrodes for establishment of the cross-gel electric field and channels for hydrodynamic pumping of flow through buffer can thus enable efficient and reproducible extraction of intact proteins from SDS-PAGE gels.

The gel electroelution device/process can thus alleviate previously described problems which can be associated with extraction of proteins from the SDS-PAGE gel matrix. For example, the gel electroelution device/process is designed to work with gels that have not been chemically fixed prior to staining (e.g., modified Coomassie blue and SYPRO orange stains). The elimination of the fixation step allows the proteins to remain in a soluble state within the gel matrix. The gel electroelution process can basically comprise a two-step process. First, an applied electric field is combined with a flow though buffer to create a much more effective vehicle for extracting the proteins from the gel spot. The buffer can mimic the natural running buffer of the SDS-PAGE gel separation, and allows the electroelution process to essentially migrate the protein off of the gel spot in the gel electroelution device. Second, the flow through buffer can then carry the extracted proteins from the electroelution device through fluidic tubing into a collection reservoir or onto a solid phase extraction trapping column, and/or, e.g., to a flow separation device for further processing. Ultimately, the extracted intact protein can be analyzed by the method of choice for the specific investigation.

Figure 5:
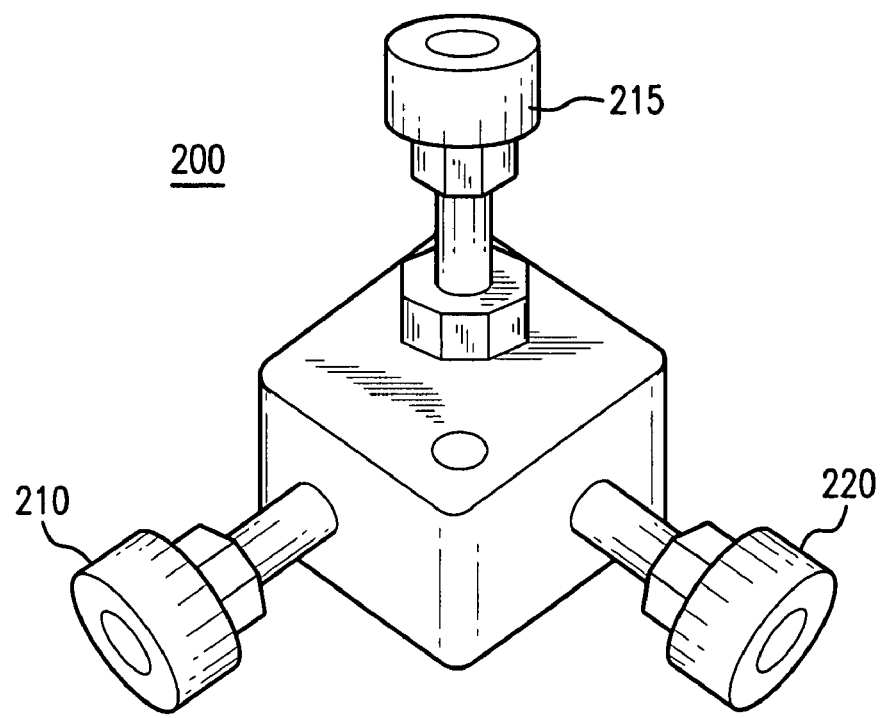
FIG. 5 is a perspective view of an embodiment of a separator device.
Figure 6:
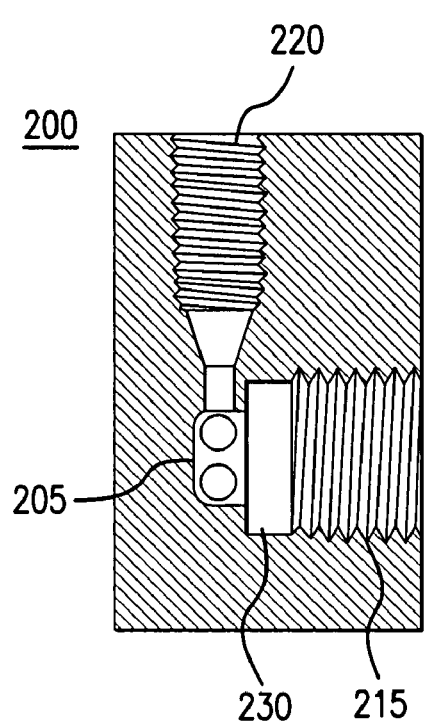
FIG. 6 is a horizontal sectional view of the separator device shown in FIG. 5.
Figure 7:
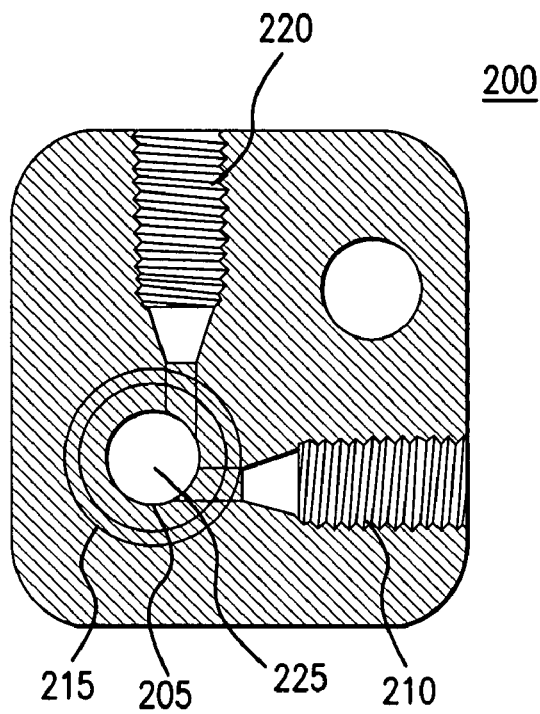
FIG. 7 is a vertical sectional view of the separator device shown in FIG. 5.

Referring now to FIGS. 5 through 7, there is illustrated an embodiment of a flow separator device 200 which can generally comprise a collection reservoir 205 in fluid communication with an inlet port 210, a filtrate port 215, and a retentate port 220. A filter receptacle 225 can be provided intermediate the inlet port 210 and the filtrate port 215. The separator device 200 can be, for example, a protein filter, and the filter receptacle 225 can receive, for example, a MWCO membrane. The collection reservoir 205 can be generally cylindrical, and each of the inlet port 210 and retentate port 220 can intersect the collection reservoir 205 in a generally tangential orientation, such that a cyclonic flow is induced in the collection reservoir 205. More particularly, the inlet 210 and retentate 220 ports can intersect the collection reservoir 205 in the off-center, generally orthogonal orientation illustrated. The fluid communication between each port 210, 220 and the collection reservoir 205 can be selectively controlled by appropriate valves (not shown). In further embodiments, the inlet 210, retentate 220 and filtrate 215 ports can be marked with different colors to easily and quickly distinguish each port.

Referring particularly to FIGS. 6 and 7, horizontal and vertical sectional views of the separator device 200 show that a shoulder 230, where the MWCO membrane seals against, is positioned adjacent the filtrate port 215, and hence all filtrate has passed through the MWCO membrane. It can be seen in these views that the inlet port 205 and the retentate port 220 intersect the collection reservoir 205 (visible in broken lines in FIG. 7) generally tangentially, e.g., in the aforesaid off-center, generally orthogonal orientation. In a filtering stage, the retentate port 220 can be closed and the filtrate port 215 opened, and the sample solution is flowed into the collection reservoir 205, via the inlet port 210, which can be located, for example, underneath the MWCO membrane, which would be received in the filter receptacle 225. The pressure of the sample solution entering the collection reservoir 205 creates hydrodynamic pressure which pushes bulk solution and other molecules of a size smaller than the MWCO upwards through the pores of the MWCO membrane and out through the filtrate port 215. Molecules of a size larger than the MWCO are retained in the collection reservoir 205. It is known that proteins and other molecules larger than the MWCO can become lodged in the membrane pores, or adsorbed into the membrane surface, which can lead to fouling of the membrane. However, the off-center, orthogonal orientation of the inlet flow creates a tangential, or sweeping, flow in the collection reservoir 205 that can prevent proteins from experiencing a static downward pressure at the membrane surface, thus reducing clogging events in the pores. Additionally, the tangential flow design improves flushing out of the collection reservoir 205 during retentate collection. The geometry of the inlet port 210 and the retentate port 220 connection to the collection reservoir 205 induces a cyclonic flow in the collection reservoir 205 during retentate collection, similar to the cyclonic flow when a commode is flushed. The cyclonic action produces a high tangential flow that helps to sweep adsorbed and lodged proteins from the membrane surface, thus improving protein sample recovery. The filter can be, for example, any conventional MWCO membrane. Typical filters of this type are paper discs with a polymer coating, such as a multi-layer polymer coating, on the side of the filter facing the collection reservoir 205. Pore size and compatibility features for such MWCO filters are well known, and filters of this type are available, for example, from Pall Corporation, of Ann Arbor, Mich. Alternative types of filters can also be used. For concentration, fractionation, and purification of proteins in the in-line filtration device, there are several membrane options that are available. Known ultrafiltration membranes are fabricated from several materials, including polyethersulfone (PES), polyvinylidene fluoride (PVDF), cellulose acetate, nylon, and cellulose nitrate. Ultrafiltration membranes are characterized by having a nominal molecular weight cut-off (MWCO) that determines the size of biological molecules that will be trapped with at least 95% efficiency on the surface of the membrane (retentate), with smaller molecules passing through the membrane as filtrate. The chemistry of the membrane and the MWCO pore size determine the types of molecules that can be separated, as well as the chemical compatibility of the device for using with other chemical reagents. Other types of membranes can also be used in the in-line filtration device, including dialysis membranes, which are fabricated from materials such as regenerated cellulose and cellulose acetate. Dialysis membranes are useful for samples that may have a high affinity for ultrafiltration membranes and adsorb tightly to their surfaces. Additionally, their chemical compatibilities are different due to their chemistry and construction, making them more useful for special experimental conditions. Ultrafiltration and dialysis membranes are commercially available from many common vendors and suppliers.

An embodiment of a flow separation process can generally comprise flowing a fluid sample into a collection reservoir, inducing a generally cyclonic flow in the collection reservoir, filtering the fluid sample using hydrodynamic pressure, and retaining retentate in the collection reservoir. Additional embodiments of the separation process can further comprise flowing a solution into the collection reservoir containing the retentate, and flowing the solution and retentate out of the collection reservoir for further processing, analysis, or storage. Further embodiments of the process can comprise rinsing, desalting, purifying, and/or concentrating the retentate in the collection reservoir. Fluorescent labeling of the retentate in the collection reservoir, and/or reduction/alkylation of proteins prior to enzymatic digestion, can also be performed.

The separator device/process can assist researchers in the concentration, purification, and preparation of protein samples for analysis. The separator device/process, which can utilize tangential fluid flow, can employ the MWCO membrane to effectively act as a sieve for biological sample solutions. Analytes and solvent molecules of a size below the MWCO will pass through the membrane as the filtrate, while sample molecules of a size above the MWCO are retained in the collection reservoir as the retentate. Inside the collection reservoir, the retentate can be rinsed, desalted, purified, and/or concentrated. Additionally, the collection reservoir can be used as a reaction chamber for fluorescent labeling of proteins and/or for reduction/alkylation of proteins prior to enzymatic digestion. Using an appropriate reagent, the separator device can also be used to remove SDS detergent from proteins trapped in the collection reservoir. Moreover, all operations can be performed in-line with a sample collection reservoir or trapping column. Sample solution addition and all rinse solutions can be added through tubing connections to the retentate port. The closed nature of the separator device can reduce the risk of chemical contamination and of handling/transfer-associated sample losses. In-line sample processing can also enable direct delivery of the concentrated and purified sample to an LC-MS column. Variable plumbing connections utilizing a standard switching valve can enable collection of either the retentate or the filtrate for subsequent analysis.

Figure 8:
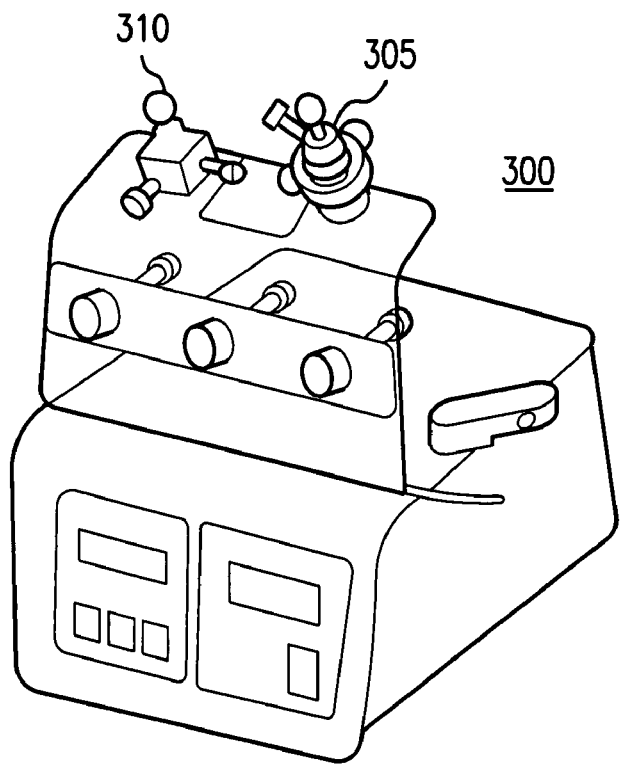
FIG. 8 is front perspective view of an embodiment of a combined gel electroelution and separator device.
Figure 9:
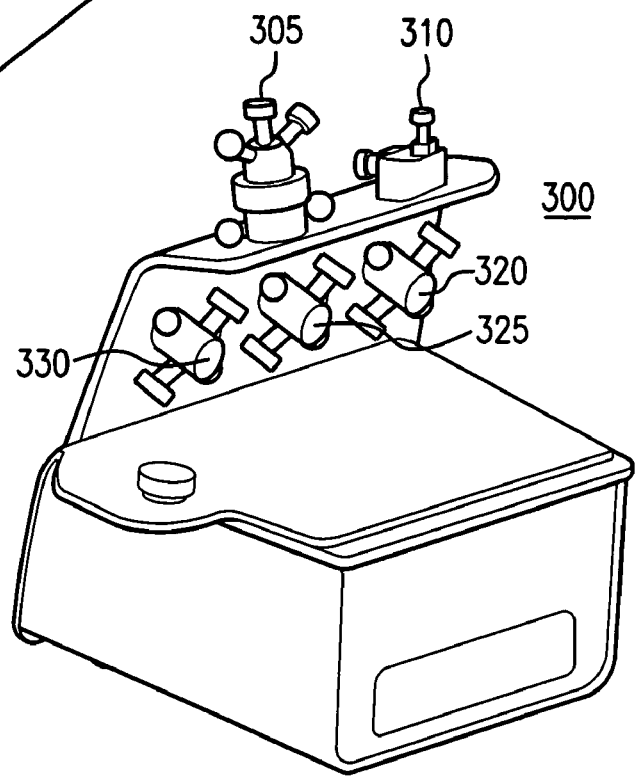
FIG. 9 is a rear perspective view of the combined gel electroelution and separator device shown in FIG. 8.
Figure 10:
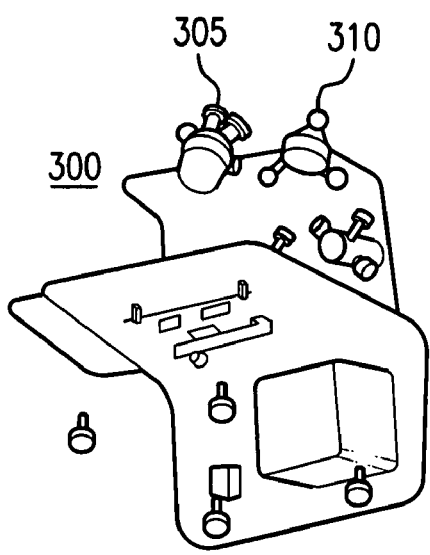
FIG. 10 is a bottom perspective view of the combined gel electroelution and separator device shown in FIG. 8, with the bottom housing removed.

Referring now to FIGS. 8-10, the gel electroelution and sample separation devices described can be used individually or can also be combined into a single integrated, stand-alone device 300, in which a continuous sample preparation process can be carried out efficiently while protecting the sample as much as possible from contamination during processing. As illustrated in FIGS. 8-10, the stand-alone device 300 can comprise an embodiment of a gel electroelution device 305 and an embodiment of a separator device 310, which devices can be, for example, the gel electroelution device 5, 100, and the separator device 200 described previously. The gel electroelution device 305 and separator device 310 can be fluidly connected using appropriate tubing, and the fluid communication, both internally and between the two devices 305, 310, can be controlled by appropriate valves, such as valves 320, 325 and 330 (which can be conventional valves), which are shown best in FIG. 9. The stand-alone device 300 can include conventional control components, such as appropriate electronic circuitry and a processor which are used in a conventionally known manner to control the gel electroelution device 305 and separator device 310, and the various fluid inter-connections therein and therebetween. These control components can also include (but are not limited to) sensors for monitoring real-time current within the electroelution device, timers for control of the electroelution applied voltage time, and a LCD or analog display for visualization of the magnitude and value of these parameters. The switching valves on the device can be used to change the fluid paths among syringes that inject buffer solutions into the fluid path, the various fluid pathways within the electroelution device, the fluid pathways of the in-line separator device, tubes for the collection of wastes, and tubes for the collection of the extracted protein samples.

Conventionally, any functionalities similar to the present gel electroelution device and separator device were performed off-line. Consequently, an embodiment of a stand-alone device comprising both of these devices is more than a mere automation of previously disparate operations: use of these two devices in an in-line fashion benefits enormously from a continuous flow system and the efficiency which continuous wet processing affords, as contrasted with largely dry separations in centrifuges known in the prior art.

Although the invention has been described with particularity above, with reference to particular structures, materials and methods, the invention is to be limited only insofar as is set forth in the accompanying claims.

What is claimed is:

1. A gel electroelution process to extract electrophoretically separated intact proteins from a gel matrix, said process comprising:

a. immobilizing a gel spot from said gel matrix, said gel spot containing said proteins to be extracted;
  b. flowing a buffer solution through said gel spot in a first direction; and
  c. creating an electric field across said gel spot in said first direction, such that said proteins electrophoretically migrate out of said gel spot and into said buffer solution.

2. The gel electroelution process of claim 1 further comprising preventing admixing of flow on upstream and downstream sides of said gel spot.

3. The gel electroelution process of claim 1 wherein said gel matrix is an SDS-PAGE gel matrix, and said buffer solution mimics a natural running buffer of said SDS-PAGE gel separation.

4. The gel electroelution process of claim 3 wherein said SDS-PAGE gel matrix has not been chemically fixed prior to staining.

5. The gel electroelution process of claim 1 further comprising filtering said buffer solution downstream of said gel spot to remove particles of gel.

6. The gel electroelution process of claim 1 further comprising collecting migrated proteins in a reservoir.

7. The gel electroelution process of claim 1 further comprising collecting the migrated proteins in a solid phase extraction trapping column.

8. A gel electroelution device comprising:

a. a gel spot column having upstream and downstream openings, said gel spot column adapted to receive therein a gel spot containing proteins to be extracted therefrom;
  b. an inlet in fluid communication with said upstream opening of said gel spot column;
  c. an outlet in fluid communication with said downstream opening of said gel spot column;
  d. a negative electrode in fluid communication with said inlet;
  e. a positive electrode in fluid communication with said outlet; and
  f. wherein said positive and negative electrodes are operable to create an electric field across said gel spot in the same direction as a flow of buffer solution from said inlet through said outlet in order to electrophoretically migrate said proteins out of said gel spot and into said buffer solution.

9. The gel electroelution device of claim 8 further comprising a frit plug intermediate said gel spot and said outlet.

10. The gel electroelution device of claim 8 further comprising a purge line in fluid communication with said gel spot column intermediate said gel well and said outlet.

11. The gel electroelution device of claim 8 further comprising a housing, and said gel spot column removably enclosed in said housing.

12. The gel electroelution device of claim 11 wherein said gel spot column further comprises a gel spot cutter, such that when said gel spot cutter is used to cut a gel spot, said gel spot is retained in said gel spot cutter, and said gel spot cutter is then enclosable in said housing with said gel spot retained therein.

* * * * *